United States Patent
Nakano et al.

(10) Patent No.: US 7,412,871 B2
(45) Date of Patent: Aug. 19, 2008

(54) OXIDIZING GAS SENSOR AND PRODUCTION METHOD THEREOF

(75) Inventors: Yoshihiro Nakano, Aichi (JP); Masahito Kida, Aichi (JP); Shinichi Nakagawa, Aichi (JP); Takio Kojima, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 154 days.

(21) Appl. No.: 11/359,380

(22) Filed: Feb. 23, 2006

(65) Prior Publication Data

US 2006/0196248 A1 Sep. 7, 2006

(30) Foreign Application Priority Data

| Feb. 24, 2005 | (JP) | 2005-049295 |
| Jun. 23, 2005 | (JP) | 2005-183171 |
| Jan. 11, 2006 | (JP) | 2006-003692 |

(51) Int. Cl.
*G01N 7/00* (2006.01)
(52) U.S. Cl. ........................................ 73/23.2
(58) Field of Classification Search ............... 73/23.2
See application file for complete search history.

(56) References Cited

U.S. PATENT DOCUMENTS

| 4,358,951 A | 11/1982 | Chang |
| 5,051,394 A * | 9/1991 | Haruta et al. ............... 502/324 |
| 5,217,692 A | 6/1993 | Rump et al. |
| 5,756,207 A * | 5/1998 | Clough et al. ............... 428/375 |

FOREIGN PATENT DOCUMENTS

| DE | 40 20 113 A1 | 1/1992 |
| EP | 1 568 990 A1 | 8/2005 |
| JP | 5-223769 A | 8/1993 |
| JP | 6-50919 A | 2/1994 |
| JP | 6-213853 A | 8/1994 |
| JP | 3097234 B2 | 8/2000 |
| WO | WO 2004/048957 A1 | 6/2004 |

OTHER PUBLICATIONS

J. Mizsei et al.; "Structural transformations of ultra-thin sputtered Pd activator layers on glass and $SnO_2$ surfaces"; Thin Solid Films; vol. 391; 2001; pp. 209-215.

V.A. Chaudhary et al.; "Selective hydrogen sensing properties of surface functionalized tin oxide"; Sensors and Actuators B; vol. 55; 1999; pp. 154-160.

(Continued)

*Primary Examiner*—Michael Cygan
(74) *Attorney, Agent, or Firm*—Sughrue Mion, PLLC (57) ABSTRACT

There is provided an oxidizing gas sensor that includes an insulating substrate, a gas sensing layer laminated on the insulating substrate and substantially made of tin oxide so as to make resistance changes in response to concentration variations in oxidizing gas and a plurality of catalyst grains applied to a surface of the gas sensing layer and substantially made of gold, wherein 20% or more of the catalyst grains have an aspect ratio of 2.0 or greater when viewed at from the surface of the gas sensing layer.

9 Claims, 7 Drawing Sheets

OTHER PUBLICATIONS

I. Hotovy et al.; "Enhancement of $H_2$ sensing properties of NiO-based thin films with a Pt surface modification"; Sensors and Actuators B; vol. 103; 2004; pp. 300-311.

N. Lopez et al.; "The adhesion and shape of nanosized Au particles in a Au/$TiO_2$ catalyst"; Journal of Catalysis; vol. 225; 2004; pp. 86-94.

Charles T. Campbell; "Metal films and particles on oxide surfaces: Structural, electronic and chemisorptive properties"; J. Chem. Soc., Faraday Trans.; vol. 92; 1996; pp. 1435-1445.

M.S. Chen et al.; "Structural-activity relationships in supported Au catalysts"; Catalysis Today; vol. 111; 2006; pp. 22-33.

J. Wöllenstein et al.; "Materials properties and the influence of metallic catalysts at the surface of highly dense $SnO_2$ films"; Sensors and Actuators B; vol. 70; 2000; pp. 196-202.

L.J. LeGore et al.; "Aggregation and sticking probability of gold on tungsten trioxide films"; Sensors and Actuators B; vol. 76; 2001; pp. 373-379.

* cited by examiner

EXAMPLE 1

FIG.5

EXAMPLE 1

FIG.6

EXAMPLE 2

FIG.7

EXAMPLE 2

FIG.8

COMPARATIVE EXAMPLE

FIG.11
EXAMPLE 1

FIG.12
EXAMPLE 2

FIG.13

COMPARATIVE EXAMPLE

OXIDIZING GAS SENSOR AND PRODUCTION METHOD THEREOF

BACKGROUND OF THE INVENTION

The present invention relates to an oxidizing gas sensor having a gas sensing layer formed of a metal oxide semiconductor material on an insulating substrate so as to make resistance changes in concentration variations in oxidizing gas. The present invention also relates to an oxidizing gas production method.

There are known various metal oxide semiconductor gas sensors, each of which includes a sensor element that features a gas sensing layer formed of a metal oxide semiconductor material on an insulating substrate to detect concentration variations in oxidizing gas such as nitrogen oxide (NOx) in response to resistance changes in the gas sensing layer due to the transfer of electrons in a surface portion of the gas sensing layer.

In one type of metal oxide semiconductor gas sensor, the sensor element has a catalyst portion in contact with the gas sensing layer, as disclosed in International Publication WO 2004/048957A1, for improvement in gas detection performance.

SUMMARY OF THE INVENTION

The metal oxide semiconductor gas sensor generally presents a drawback that the resistance of the sensor element changes over time. In order to overcome such a drawback and improve the resistance stability of the sensor element, it is conceivable to subject the sensor element to heat treatment at temperatures of 350° C. or higher in a flow of vapor-containing air as proposed in Japanese Laid-Open Patent Publication No. 6-213853. The adhesion of the catalyst portion to the gas sensing layer may however become weakened depending on the high-temperature heat treatment conditions due to the fact that the proposed heat treatment is not intended for the metal oxide semiconductor gas sensor of the type in which the catalyst portion is in contact with the gas sensing layer and gives no consideration to the adhesion of the catalyst portion to the gas sensing portion. It is very likely that a separation of the catalyst portion from the gas sensing layer will occur over the course of time when the adhesion of the catalyst portion to the gas sensing layer is weakened. This result in a deterioration of the sensitivity and durability of the sensor element.

It is therefore an object of the present invention to provide a gas sensor having a gas sensing layer formed of a metal oxide semiconductor material on an insulating substrate and a catalyst portion formed of a noble metal in contact with the gas sensing layer without causing a weakening of the adhesion between the gas sensing layer and the catalyst portion even during long term use.

It is also an object of the present invention to provide a gas sensor production method.

According to one aspect of the present invention, there is provided a gas sensor, comprising: an insulating substrate; a gas sensing layer laminated on the insulating layer and substantially made of tin oxide so as to make resistance changes in response to concentration variations in oxidizing gas; and a plurality of catalyst grains applied to a surface of the gas sensing layer and substantially made of gold, wherein 20% or more of the catalyst grains having an aspect ratio of 2.0 or greater when viewed at from the surface of the gas sensing layer.

According to another aspect of the present invention, there is provided a method of producing a gas sensor, comprising: forming a gas sensing layer of tin oxide on an insulating substrate by a thin-film formation process; applying, without adding heat to the insulating substrate, a plurality of catalyst grains of gold to a surface of the gas sensing layer by a thin-film application process; and heat treating the gas sensing layer and the catalyst grains in an atmosphere with an oxygen content of 10 ppm or lower.

The other objects and features of the present invention will also become understood from the following description.

DESCRIPTION OF THE EMBODIMENTS

An oxidizing gas sensor 1 according to one embodiment of the present invention will be described below with reference to the drawings. It is noted that, for explanation purposes, the gas sensor 1 is specifically designed to detect the concentration of oxidizing gas, notably nitrogen dioxide ($NO_2$), in a gaseous material under measurement.

Figure 1:
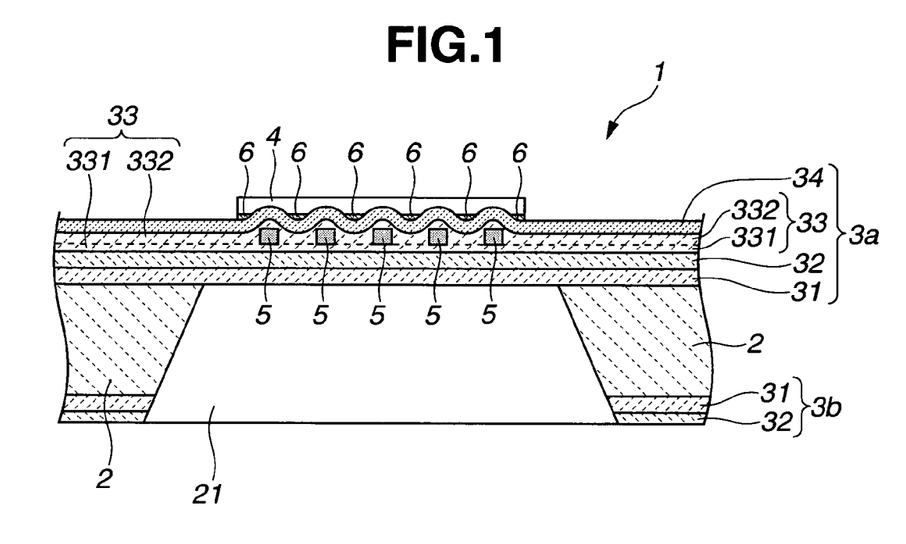
FIG. 1 is a sectional view of an oxidizing gas sensor according to one exemplary embodiment of the present invention.
Figure 2:
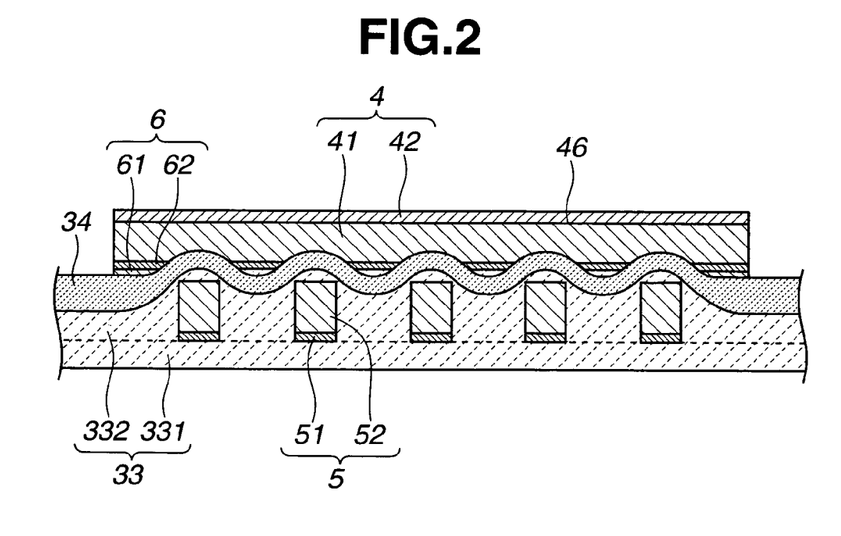
FIG. 2 is a sectional view of a sensor element of the oxidizing gas sensor according to one exemplary embodiment of the present invention.

As shown in FIGS. 1 and 2, the gas sensor 1 includes an insulating substrate and a sensor element 4 having a gas sensing layer 41 laminated on the insulating substrate and formed of a metal oxide semiconductor material and a catalyst portion 42 held in contact with the gas sensing layer 41 and formed of a noble metal. The insulating substrate is herein a laminated composite of a substrate core 2 and insulating film layers 3a and 3b, and the sensor element 4 is of rounded rectangular plane form. In the present embodiment, the gas sensing layer 41 is substantially made of tin oxide ($SnO_2$), i.e., contains tin oxide as the main component in an amount of 99% or greater based on the total mass of the gas sensing layer 41. By contrast, the catalyst portion 42 consists of a plurality of grains that are substantially made of gold (Au) and applied to and scattered over a surface 46 of the gas sensing layer 41 located on the opposite side of the gas sensing layer 41 from the insulating substrate in the present embodiment.

The grains of the catalyst portion 42 (hereinafter just referred to as "catalyst grains") include three-dimensional spherical grains that are uniform in diameter (of perfect or nearly perfect sphere shape) and three-dimensional non-spherical grains that are not uniform in diameter (of e.g. oval sphere shape). In general, the non-spherical catalyst grains provide a larger contact area than the spherical catalyst grains so as to achieve better adhesion of the catalyst portion 42 to the gas sensing layer 41.

Accordingly, the catalyst portion 42 is controlled in such a manner that 20% or more of the catalyst grains have an aspect ratio of 2.0 or greater when viewed at from the surface 46 of the gas sensing layer 41. The catalyst grains having an aspect ratio of 2.0 or greater are non-spherical in shape and provide a relatively large area of contact between the gas sensing layer 41 and the catalyst portion 42. When the percentage of the non-spherical catalyst grains is controlled to the above-specified high percentage range, the sensor element 4 can improve the adhesion between the gas sensing layer 41 and the catalyst portion 42 and prevent separation of the catalyst portion 42 from the gas sensing layer 41.

Figure 3:
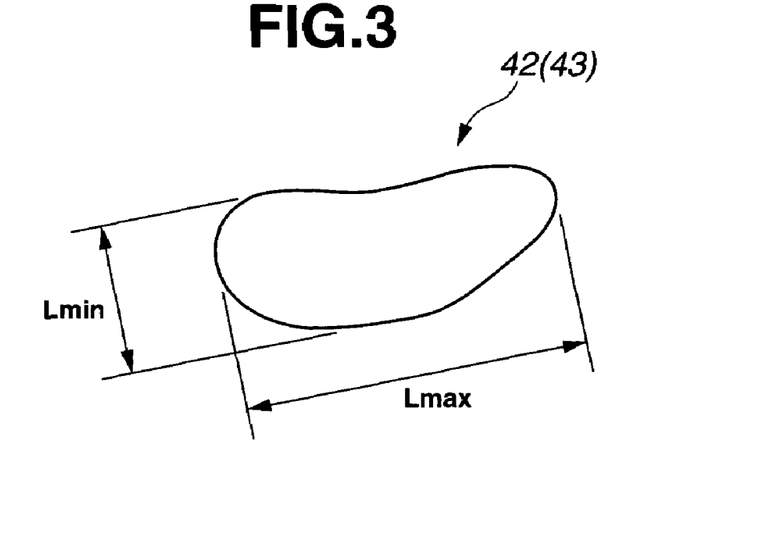
FIG. 3 is a schematic view showing how to measure catalyst grain dimensions of the sensor element according to one exemplary embodiment of the present invention.

In the present embodiment, the aspect ratio is defined as a length-to-width ratio of the catalyst grain and determined by taking a SEM picture with a scanning electron microscope (FE-SEM) from the surface of the gas sensing layer 41, and then, observing an image of the catalyst grains in the SEM picture. The picture magnification and area are selected appropriately such that the taken picture contains the image of a plurality of catalyst grains (preferably about 100 catalyst grains). One example of non-spherical catalyst grain 43 is shown in FIG. 3. In the case of the non-spherical catalyst grain 43, the aspect ratio is calculated by dividing the longest dimension Lmax of the catalyst grain 43 by the maximum dimension Lmin of the catalyst grain 43 in a direction perpendicular to the direction of the longest dimension Lmax as shown in FIG. 3

When the gas sensing layer 41 is relatively large in thickness, the catalyst grains can exist on and in the surface 46 of the gas sensing layer 41 so that a separation of the catalyst portion 42 from the gas sensing layer 41 is unlikely to occur in the presence of some catalyst grains in the gas sensing layer 41. On the other hand, substantially all of the catalyst grains exist on the surface 46 of the gas sensing layer 41 when the gas sensing layer 41 is relatively small in thickness. Even in such a case, the sensor element 4 can secure good adhesion between the gas sensing layer 41 and the catalyst portion 42 and prevent separation of the catalyst portion 42 from the gas sensing layer 41 through the effects of the aspect ratio control of the catalyst grains. In other words, the aspect ratio control of the catalyst grains is effective in both of the cases where the catalyst grains exist on and in the surface 46 of the gas sensing layer 41 and where the catalyst grains exist on the surface 46 of the gas sensing layer 41.

In order to secure better adhesion between the gas sensing layer 41 and the catalyst portion 42 and prevent separation of the catalyst portion 42 from the gas sensing layer 41 more effectively, it is desirable to control the percentage of the catalyst grains having an aspect ratio of 2.0 or greater to 30% or more, especially 40% or more.

It is also desirable to control the percentage of the catalyst grains having an aspect ratio of smaller than 1.1 to 10% or less, more desirably 5% or less, especially 3% or less. The catalyst grains having an aspect ratio of smaller than 1.1 are spherical or roughly spherical in shape and provide a relatively small area of contact between the gas sensing layer 41 and the catalyst portion 42. If the percentage of such spherical catalyst grains is large, the adhesion between the gas sensing layer 41 and the catalyst portion 42 becomes poor so that a separation of the catalyst portion 42 from the gas sensing layer 41 is likely to occur. When the percentage of the spherical catalyst grains is controlled to the above-specified low percentage range, however, the sensor element 4 can avoid poor adhesion between the gas sensing layer 41 and the catalyst portion 42 and prevent separation of the catalyst portion 42 from the gas sensing layer 41 effectively.

It is further desirable that at least some of the catalyst grains are at least partially flat in shape so as to provide a larger contact area, secure better adhesion between the gas sensing layer 41 and the catalyst portion 42 and prevent separation of the catalyst portion 42 from the gas sensing layer 41.

Herein, at least part of the surface 46 of the gas sensing layer 41 needs to be exposed to the outside of the gas sensor 1, without the gas sensing layer surface 46 being totally covered by the catalyst portion 42, so as to allow the oxidizing gas to be detected to reach the gas sensing layer surface 46 and thereby cause electron transfer in a surface portion of the gas sensing layer 41. The catalyst grains make a large contribution to the electron transfer in the surface portion of the gas sensing layer 41 for improvement in gas detection performance when at least partially exposed to the outside of the gas sensing layer 41, but make little contribution to the electron transfer in the surface portion of the gas sensing layer 41 when totally embedded in the gas sensing layer 41. It is thus preferred that, while at least part of the surface 46 of the gas sensing layer 41 is exposed to the outside of the gas sensor 1, the catalyst grains are at least partially exposed to the outside of the gas sensing layer 41, in order to enhance the electron transfer in the surface portion of the gas sensing layer 41 through the catalytic effects of the catalyst portion 42. It is thus possible to obtain improved gas detection performance without a deterioration in gas sensitivity.

For secular gas sensitivity/stability, it is desirable that the area of the surface 46 of the gas sensing layer 41 covered by the catalyst portion 42 constitute 1.5% to 93.0%, more desirably 2.0% to 90.0%, especially 2.0% to 75.0%, of the total area of the gas sensing layer surface 46.

In the present embodiment, the ratio of the area of the surface 46 of the gas sensing layer 41 covered by the catalyst portion 42 to the total area of the gas sensing layer surface 46 (hereinafter referred to as "catalyst area ratio") is determined by taking a SEM picture of the sensor element 4 with a scanning electron microscope (FE-SEM) and dividing the area of a reflected electron image of the catalyst grains in the SEM picture by the total image area of the SEM picture.

When the catalyst area ratio is controlled to within the above-specified range, the sensor element 4 can achieve high gas sensitivity. There arise no problems in the use of such a high sensitive sensor element 4 even under conditions that cause sensitivity deterioration. This makes it possible to attain secular gas detection stability without a deterioration in gas sensitivity.

It is further desirable that, for sensor reliability, the ratio of the number of gold atoms (i.e. the constituent metal element of the catalyst portion 42) to the sum of the number of tin atoms (i.e. the constituent element of the gas sensing layer 41) and the number of gold atoms at the gas sensing layer surface 46 (hereinafter referred to as a "surface atom ratio Au/(Sn+Au)") ranges from 10% to 70%, more desirably 20 to 60%.

In the present embodiment, the surface atom ratio Au/(Sn+Au) is measured by X-ray photoelectron spectroscopy (XPS). More specifically, the surface atom ratio Au/(Sn+Au) is determined by measuring the photoelectron peak areas of the respective constituent elements by an Xray surface analyzer (such as "Quantera SXM" available from Physical Electronics) using AlKα (1486 keV) as X-ray source within a detection range of 100 μm at a detection depth of 4 to 5 nm (a takeoff angle of 45°), calculating the quantities (atom numbers) of the constituent elements according to the following equation, and then, substituting these calculation values into the equation of the surface atom ratio Au/(Sn+Au):

$$Ci = \frac{(Ai/RSFi)}{(\sum iAi/RSFi)} \times 100$$

where Ci is the quantity of the element i (in units of atomic %); Ai is the photoelectron peak area of the element i; and RSFi is the relative sensitivity index of the element i.

If the surface atom ratio Au/(Sn+Au) is less than 10%, the proportion of the catalyst portion 42 on the gas sensing layer 41 is so small that the gas sensitivity of the sensor element 4 is high in the initial state but likely to deteriorate with time. If the surface atom ratio Au/(Sn+Au) exceeds 70%, the proportion of the catalyst portion 42 on the gas sensing layer 41 is so high that the gas sensitivity of the sensor element 4 is low even in the initial state. When the surface atom rate Au/(Sn+Au) is controlled to within the above-specified range, however, the gas sensitivity of the sensor element 4 can be prevented from deteriorating in the initial state and over the course of time. This makes it possible to improve the reliability of the sensor element 4.

In order to prevent a sensitivity deterioration of the sensor element 4 effectively, it is more desirable to control the surface atom ratio Au/(Sn+Au) to within a range of 20% to 60%.

As shown in FIGS. 1 and 2, the gas sensor 1 includes a heater 5 and at least one pair of electrodes 6 in addition to the insulating substrate i.e. the substrate core 2 and the insulating films 3a and 3b and the sensor element 4.

The substrate core 2 is made of silicon in the present embodiment. The insulating films 3a and 3b are arranged on opposite surfaces of the insulating substrate 2 so that the sensor element 4 is supported on the insulating film 3a. Each of the insulating films 3a and 3b has a first insulating layer 31 laminated on the substrate core 2 and a second insulating layer 32 laminated on the first insulating layer 31. In the present embodiment, the first and second insulating layers 31 and 32 are made of silicon oxide ($SiO_2$) and silicon nitride ($Si_3N_4$), respectively. The insulating film 3a also has a third insulating layer 33 laminated on the second insulating layer 32 and a fourth insulating layer 34 laminated on the third insulating layer 33. The third and fourth insulating layer portions 33 and 34 are made of silicon oxide ($SiO_2$) and silicon nitride ($Si_3N_4$), respectively, in the present embodiment.

There is an opening 21 formed, at a location corresponding to the sensor element 4 (below the sensor element 4 in FIG. 1), through the insulating substrate 2 and the insulating film 3b in thickness directions thereof such that the gas sensor 1 has a diaphragm structure.

The heater 5 is embedded within the third insulating layer 33 (i.e. arranged between lower and upper layer portions 331 and 332 of the third insulating layer 33) of the first insulating film 3a at a location adjacent to the sensor element 4 and the opening 21 (directly below the sensor element 4 and directly above the opening 21 in FIG. 1) so as to heat the gas sensing layer 41 of the sensor element 4. By the arrangement of the gas sensing layer 41, the heater 5 and the opening 21 at locations corresponding to one another, the gas sensing layer 41 can be heated by means of the heater 5 efficiently for quick and early activation of the gas sensing layer 41 and for accurate detection of the oxidizing gas. As shown in FIG. 2, the heater 5 has a double-layer structure consisting of a lower heater layer 51 arranged on the lower layer portion 331 of the third insulating layer 33 and an upper heater layer 52 laminated on the lower heater layer 51. In the present embodiment, the lower and upper heater layers 51 and 52 are made of tantalum (Ta) and platinum (Pt), respectively. Although not shown in the drawings, a heater lead is connected to the heater 5 so as to energize the heater 5 with power supply from an external device. The heater lead is formed with a contact portion for connection to the external device. Further, the heater lead has the same double-layer structure as that of the heater 5 in the present embodiment.

The electrodes 6 are arranged on the fourth insulating layer 34 of the first insulating film 3a at positions adjacent to the heater 5 in such a manner that adjacent two of the electrodes 6 forms an electrode pair and are electrically connected with the gas sensing layer 41 of the sensor element 4. Each of the electrodes 6 also has a double-layer structure consisting of a lower electrode layer 61 laminated on the fourth insulating layer 34 and an upper electrode layer 62 laminated on the lower electrode layer 61 as shown in FIG. 2. In the present embodiment, the lower and upper electrode layers 61 and 62 are made of titanium (Ti) and platinum (Pt), respectively. Further, electrode leads are connected to the electrodes 6 although not shown in the drawings. The electrode leads are formed with contact portions for connections to the external device.

With the above structure, the gas sensor 1 makes resistance changes in the gas sensing layer 41 due to the electron transfer through the surface portion of the gas sensing layer 41 in the presence of the oxidizing gas to be detected, so as to detect concentration variations in the oxidizing gas in response to such resistance changes and produce output about the oxidizing gas concentration variations to the external device.

The above-structured gas sensor 1 can be produced by forming the gas sensing layer 41 on the insulating substrate, applying the catalyst grains to the gas sensing layer 41 so as to form the catalyst portion 42 on (or on and in) the gas sensing layer 41, and then, subjecting the gas sensing layer 41 and the catalyst portion 42 to heat treatment in an atmosphere containing 10 ppm or lower of oxygen. Both of the gas sensing layer 41 and the catalyst portion 42 can be prepared by any known thin-film formation/application process such as sputtering or deposition. No heat is added to the insulating substrate during the application of the catalyst portion 42 to the gas sensing layer 41.

The resistance stability of the sensor element 4 can be improved through the heat treatment of the gas sensing layer 41 and the catalyst portion 42 (after the formation of the gas sensing layer 41 and the catalyst portion 42 on the substrate). When the heat treatment is performed in a high oxygen content atmosphere, however, the degree of agglomeration of the catalyst grains becomes so high under the effects of oxygen that the catalyst grains tend to be three-dimensionally uniform in diameter (spherical in shape). In particular, the agglomeration degree of the catalyst grains during the heat treatment is high when the catalyst grains are of gold. The catalyst portion 42 becomes prone to separation from the gas sensing layer 41 due to poor adhesion between the gas sensing layer 41 and the catalyst portion 42. In the present embodiment, however, the heat treatment is performed in the above-specified low oxygen content atmosphere. This makes it possible to control the agglomeration degree of the catalyst grains, secure an appropriate amount of non-spherical catalyst grains in the catalyst portion 42 and avoid poor adhesion between the gas sensing layer 41 and the catalyst portion 42.

In order to prevent a deterioration of the adhesion between the gas sensing layer 41 and the catalyst portion 42 effectively, it is more desirable to control the oxygen content of the heat treatment atmosphere to a lower level, e.g., 5 ppm or lower, especially 0.2 ppm or lower.

The temperature of the heat treatment atmosphere is not particularly restricted and can be set to e.g. 360° C. In order to impart secular resistance stability to the sensor element 4, the heat treatment temperature is desirably set to be some extent (e.g. 50° C.) higher than the operation temperature of the gas sensor 1 in order to achieve secular resistance stability. For example, the heat treatment temperature may be set to 300° C. or higher when the operating environment temperature of the gas sensor 1 is 250° C.

In this way, the sensor element 4 is able to attain not only secular resistance stability but also good adhesion between the gas sensing layer 41 and the catalyst portion 42. The occurrence of a separation of the catalyst portion 42 from the gas sensing layer 41 can be avoided, without a deterioration of the adhesion between the gas sensing layer 41 and the catalyst portion 42, so as to prevent changes in the resistance of the sensor element 4 over the course of time. It is therefore possible according to the present embodiment to protect the sensor element 4 from performance deterioration and improve.

The present invention will be described in more detail by reference to the following examples. However, it should be noted that the following examples are only illustrative and not intended to limit the invention thereto.

EXPERIMENT 1

Example 1

Production of Gas Sensors

A plurality of sample $NO_2$ sensors were produced in the following first through fourteenth production steps.

In the first step, a silicon wafer was immersed in a cleaner to clean surfaces of the silicon wafer.

In the second step, the silicon wafer was heat treated in a furnace to oxidize surface portions of the silicon wafer and thereby form silicon oxide layers of 100 nm thickness (as the first insulating layer 31) while leaving the remaining non-oxidized portion of the silicon wafer as a silicon core (the substrate core 2).

In the third step, silicon nitride layers of 200 nm thickness (as the second insulating layers 32) were applied to surfaces of the insulating silicon oxide layers formed in the second step, respectively, by a LP-CVD (Low Pressure Chemical Vapor Deposition) process using $SiH_2Cl_2$ and $NH_3$ as a source gas.

In the fourth step, a silicon oxide layer of 100 nm thickness (as the lower layer portion 331 of the third insulating layer 33) was applied to a surface of either one of the insulating silicon nitride layers formed in the third step, by a plasma CVD process using TEOS (tetraethoxysilane) and $O_2$ as a source gas.

In the fifth step, a double-layer heating element (as the heater 5) was prepared by applying a tantalum layers of 20 nm thickness (as the heater layer 51) with the use of a DC (Direct Current) sputtering device to a surface of the insulating silicon oxide layer formed in the fourth step, applying a platinum layer of 220 nm thickness (as the heater layer 52) to the tantalum layer with the use of a DC sputtering device, producing a resist pattern by photolithography, and then, removing the unnecessary portions of the tantalum and platinum layers by a wet etching process.

In the sixth step, a silicon oxide layer of 100 nm thickness (as the upper layer portion 332 of the third insulating layer 33) was applied to the surface of the insulating silicon oxide layer formed in the fourth step, so as to cover the heating element, by a plasma CVD process using TEOS (tetraethyl orthosilicate) and $O_2$ as a source gas.

In the seventh step, a silicon nitride layer of 200 nm thickness (as the fourth insulating layer 34) was applied to a surface of the insulating silicon oxide layer formed in the sixth step, by a LP-CVD process using $SiH_2Cl_2$ and $NH_3$ as a source gas.

In the eighth step, heater leads with contact portions were formed by producing a resist pattern by photolithography and dry etching the unnecessary portions of the insulating layers formed in fourth, sixth and seventh steps.

In the ninth step, electrode pairs (as the electrodes 6) were prepared by applying a titanium layer of 20 nm thickness (as the electrode layer 61) with the use of a DC sputtering device to a surface of the insulating silicon nitride layer given in the seventh step, applying a platinum layer of 40 nm thickness (as the electrode layer 62) to the titanium layer with the use of a DC sputtering device, producing a resist pattern by photolithography, and then, wet etching the unnecessary portions of the titanium and platinum layers. Electrode leads with contact portions were formed simultaneously with the electrode pairs.

In the tenth step, contact pads (bonding pads) for connection to the heater and electrode contact portions were prepared by applying a gold layer of 400 nm thickness, with the use of a DC sputtering device, to a portion of the surface of the insulating silicon nitride layer on where the electrode pairs had been formed, producing a resist pattern by photolithography, and then, wet etching the unnecessary portion of the gold layer.

In the eleventh step, an opening (as the diaphragm opening 21) was formed by producing a resist pattern by photolithography on the other of the insulating silicon nitride layers formed in the third step, subjecting the insulating mask layer to dry etching, and then, immersing the silicon core and the insulating layers formed in the second and third steps into a TMAH (tetramethylammonium hydroxide) solution to remove the unnecessary portions of these insulating substrate materials by anisotropic silicon etching.

In the twelfth step, a sensor element of rounded rectangular plane form (as the sensor element 4) was prepared by the following procedure. First, a tin oxide layer of 200 nm thickness (as the gas sensing layer 41) was sputtered onto a surface of the insulating silicon nitride layer formed in the seventh step, at locations corresponding to the heating element and the opening, with the use of a RF (Radio Frequency) sputtering device using tin oxide ($SnO_2$) as a target at a sputtering speed of 2 nm/min. During the tin oxide layer sputtering, the substrate was heated to 50 to 400° C. Next, gold grains (as the catalyst grains of the catalyst portion 42) were sputtered onto a surface of the tin oxide layer with the use of either a DC sputtering device or a RF sputtering device using gold (Au) as a target. No heat was added to the substrate during the gold grain sputtering.

In the thirteenth step, the laminate in which the tin oxide layer and the gold grains had been laminated on the substrate material was heat treated at 360° C. for 3 hours in an atmosphere with an oxygen content of 0.2 ppm with the use of either a RF sputtering device or a heat treatment furnace. During the heat treatment, the gold grains were agglomerated appropriately and scattered over the tin oxide layer so as not to cover the whole of the surfaces of the tin oxide layer.

Herein, the sputtering conditions of the twelfth step and the heat treatment conditions of the thirteenth step were set suitably in such a manner as to control the surface atom rate Au/(Sn+Au) to 45%.

In the fourteenth step, the substrate was cut by a dicing saw to separate the thus-obtained sample sensor from the other sample sensors. Each of the sample sensors was completed (into a gas sensor device) by being connected to a wiring board via a gold wire and subjected to aging at 250° C. for 100 hours in the air.

Performance Evaluations

The performance of the sample sensors was evaluated as follows.

Figure 4:
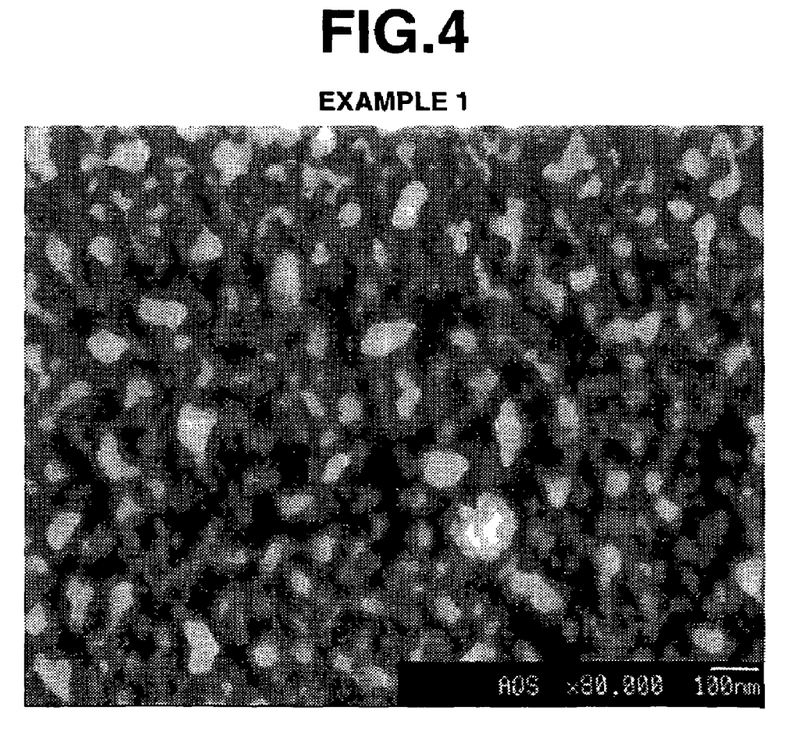
FIG. 4 is a SEM picture of a gas sensor element of Example 1.

A SEM picture of the tin oxide layer and the gold grains was taken as an reflected electron image by a field emission scanning electron microscope (FE-SEM) with a magnification of 80,000 times and an acceleration voltage of 5 kV. The reflected electron image of the tin oxide layer and the gold grains is shown in FIG. 4. In the reflected electron image of FIG. 4, the surface of the tin oxide layer and the gold grains are seen in dark (black) and light (white) colors, respectively.

Figure 5:
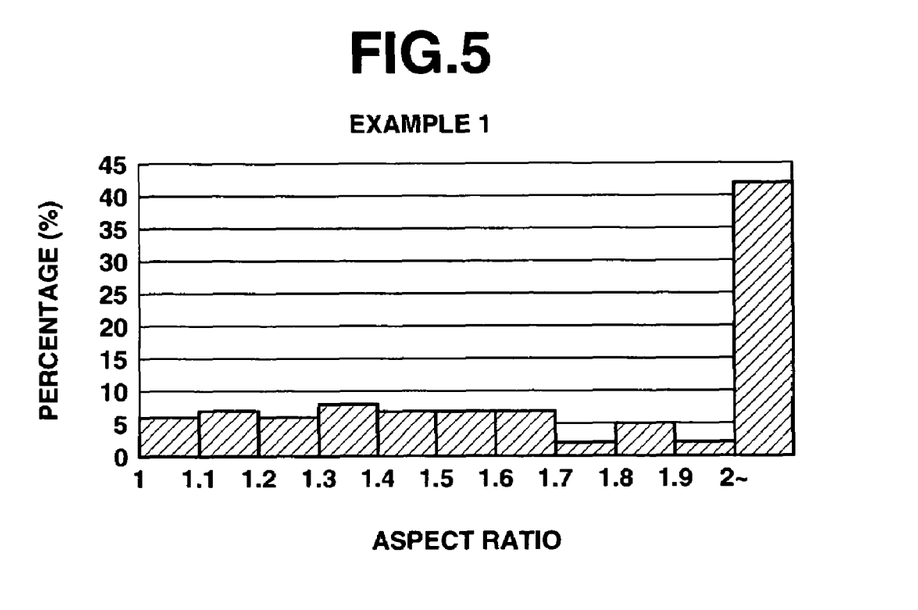
FIG. 5 is a bar chart showing an aspect ratio distribution of catalyst grains of the sensor element of Example 1.

As is apparent from FIG. 4, the gold grains were scattered over the surface of the tin oxide layer and not kept in absolute contact with one another so that the surface of the tin oxide layer was partially exposed to the outside through gaps among the gold grains. Further, the gold grains were of varying three-dimensional shapes (spherical and non-spherical shapes) but generally angular and at least partially flat in shape as is seen in FIG. 4. The aspect ratio of each of 100 gold grains in an arbitrary area of the SEM picture was determined according to the above-defined method. A distribution of the aspect ratios of the gold grains is indicated in FIG. 5 in the form of a 1-segment bar chart (in increments of 0.1). The percentage of non-spherical gold grains having an aspect ratio of 2.0 or greater was about 41%, and the percentage of spherical gold grains having an aspect ratio of smaller than 1.1 was about 6%.

Chemical element analysis was next performed on the surface of the tin oxide layer by XPS according to the above-defined method. Both of Sn and Au atoms were detected through XPS observation. It means that the gold grains were scattered over the surface of the tin oxide layer without covering the whole of the surface of the tin oxide layer. The surface atom rate Au/(Sn+Au) of the sensor element was calculated to be 45% according to the above-defined method.

Figure 10:
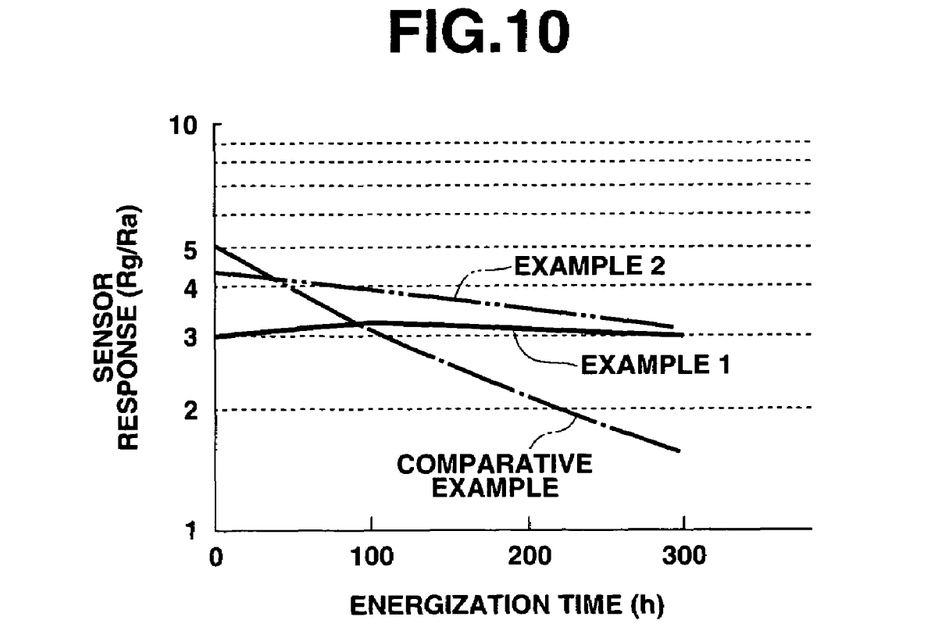
FIG. 10 is a graph showing a gas sensitivity comparison of the sensor elements of Example 1, Example 2 and Comparative Example.

Further, the energization durability of the sensor element was tested by detecting an electrical resistance Ra of the tin oxide layer during the flow of a base gas (referred to as a "reference resistance value") and an electrical resistance Rg of the tin oxide layer after a lapse of 5 seconds from the addition of 1 ppm of $NO_2$ gas (referred to as a "gas-detecting resistance value") and calculating a sensor response Rg/Ra by the division of the gas-detecting resistance value Rg by the reference resistance value Ra. Herein, a mixture of 20.9% oxygen ($O_2$) and the balance being nitrogen ($N_2$) having a relative gas humidity of 40% was used as the base gas, and the gas temperature and the heating element temperature were set to 25° C. and 200° C., respectively, during the resistance measurement. A larger value of the sensor response Rg/Ra means a higher gas detection rate, i.e., a higher gas sensitivity, whereas a smaller value of the sensor response Rg/Ra means a lower gas detection rate, i.e., a lower gas sensitivity. A variation in the sensor response Rg/Ra with respect to the energization time is indicated in FIG. 10. As is apparent from FIG. 10, the sensor response Rg/Ra was stable at about 3.0 with little change during a lapse of 300 hours after the initiation of energization.

Figure 11:
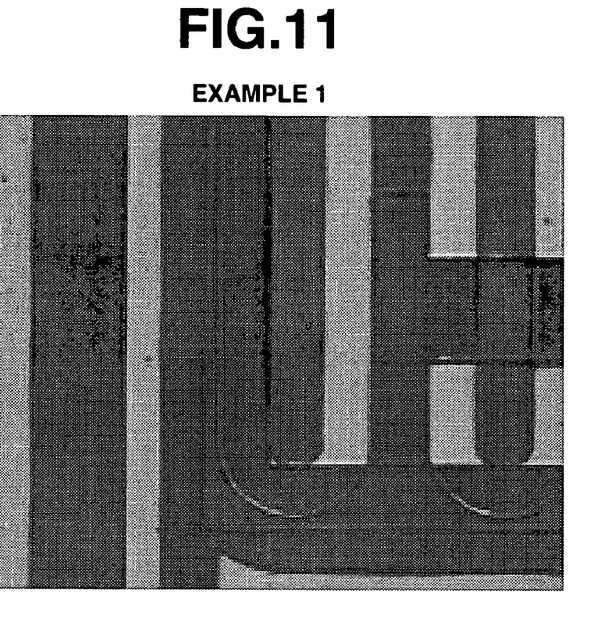
FIG. 11 is an optical microscope photograph of the sensor element of Example 1.

After the testing of the sensor response Rg/Ra, a photograph of the tin oxide layer and the gold grains was taken by an optical microscope to examine the occurrence of a separation of the gold grains from the tin oxide layer. The photograph of the tin oxide layer and the gold grains is shown in FIG. 11. No separation of the gold grains from the tin oxide layer was observed as in FIG. 11.

The above evaluation results were summarized in TABLE 1.

Example 2

In Example 2, sample $NO_2$ sensors were produced in the same manner as in Example 1, except that the oxygen content of the heat treatment atmosphere in the thirteenth step was controlled to 5 ppm.

The performance of the sample sensors was then evaluated in the same manner as in Example 1.

Figure 6:
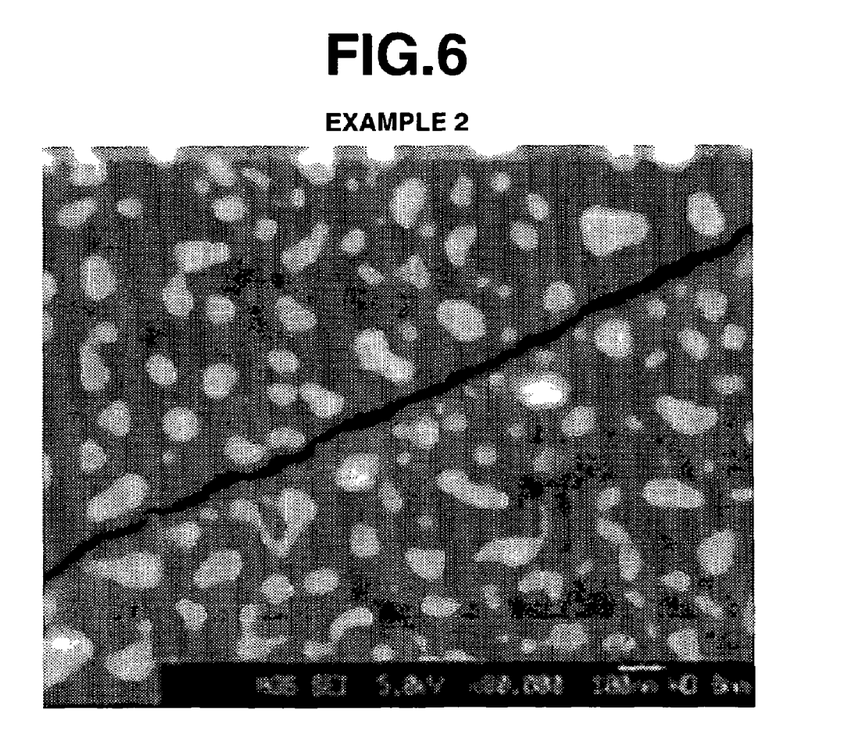
FIG. 6 is a SEM picture of a gas sensor element of Example 2.
Figure 7:
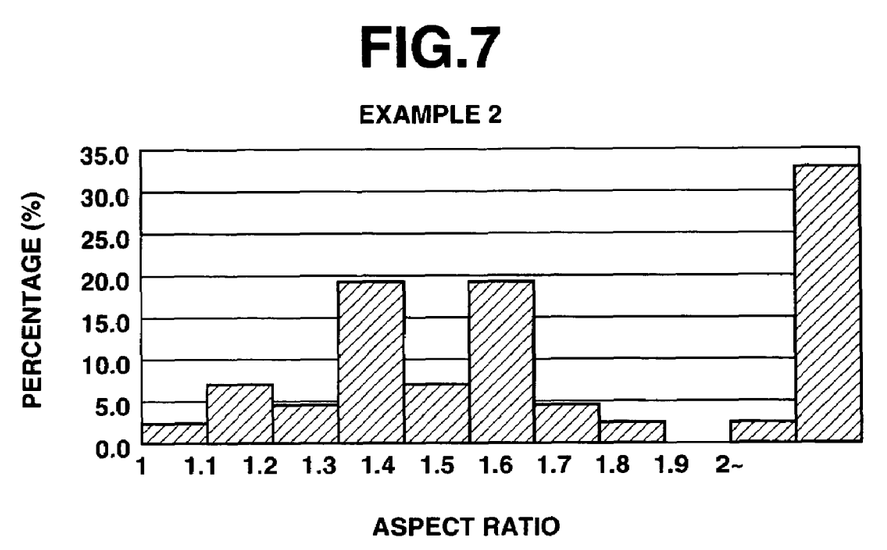
FIG. 7 is a bar chart showing an aspect ratio distribution of catalyst grains of the sensor element of Example 2.

A SEM picture of the tin oxide layer and the gold grains of Example 2 is shown in FIG. 6, and a distribution of the aspect ratios of the gold grains of Example 2 is indicated in FIG. 7. As is apparent from FIG. 6, the tin oxide layer of Example 2 was partially exposed to the outside through gaps among the gold grains. Further, the gold grains of Example 2 were also of varying three-dimensional shapes (spherical and non-spherical shapes) but less angular in shape than those of Example 1 as is seen in FIG. 6. In Example 2, the percentage of non-spherical gold grains having an aspect ratio of 2.0 or greater was about 32.5%, and the percentage of spherical gold grains having an aspect ratio of smaller than 1.1 was about 2.5%.

A variation in the sensor response Rg/Ra with respect to the energization time is indicated in FIG. 10. As is apparent from FIG. 10, the sensor response Rg/Ra was lowered only by about 1.2 during a lapse of 300 hours after the initiation of energization in Example 2.

Figure 12:
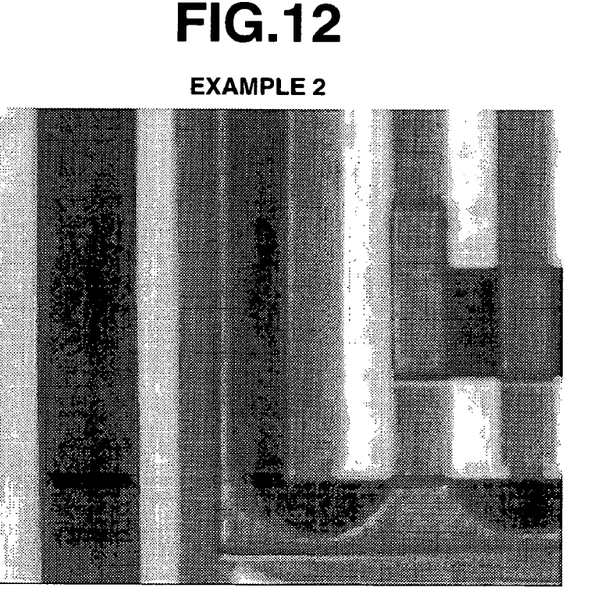
FIG. 12 is an optical microscope photograph of the sensor element of Example 2.

An optical microscope photograph of the tin oxide layer and the gold grains of Example 2 is shown in FIG. 12. In Example 2, no separation of the gold grains from the tin oxide layer was observed as in FIG. 12.

The evaluation results of Example 2 were summarized in TABLE 1.

Comparative Example

In Comparative Example, sample $NO_2$ sensors were produced in the same manner as in Examples 1 and 2, except that the heat treatment of the thirteenth step was performed in the air containing about 20% of oxygen (i.e. the oxygen content of the heat treatment atmosphere in the thirteen step was approximately 20000 ppm).

The performance of the sample sensors was then evaluated in the same manner as in Examples 1 and 2.

Figure 8:
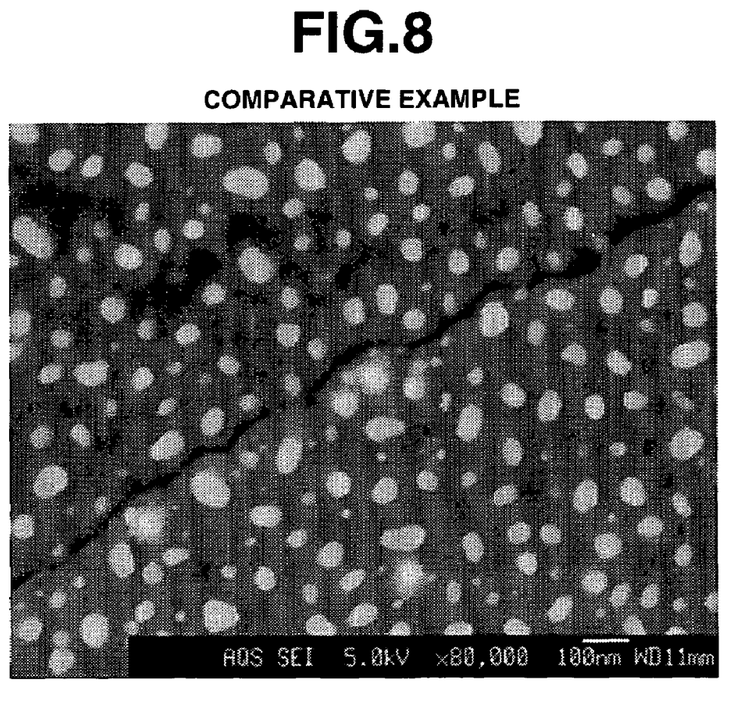
FIG. 8 is a SEM picture of a gas sensor element of Comparative Example.
Figure 9:
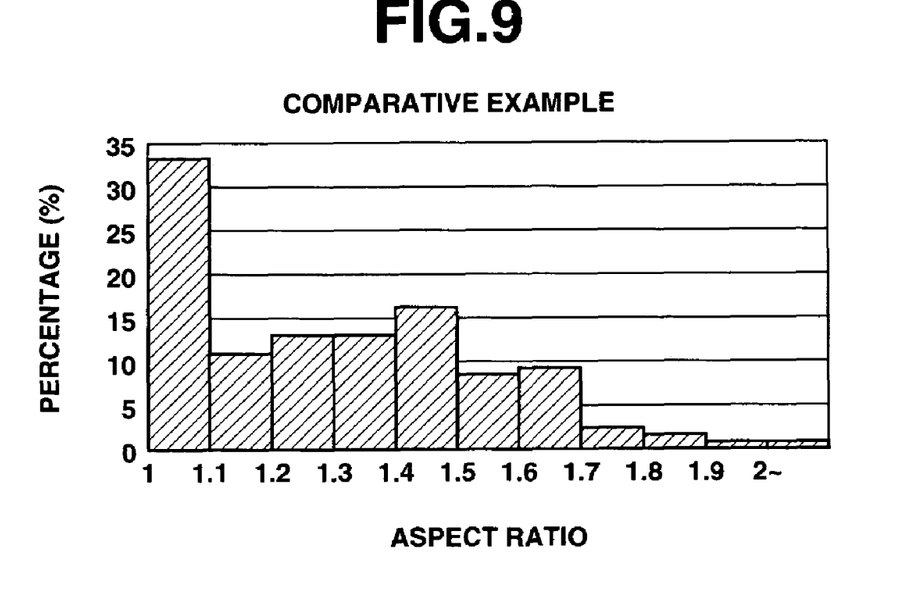
FIG. 9 is a bar chart showing an aspect ratio distribution of catalyst grains of the sensor element of Comparative Example.

A SEM picture of the tin oxide layer and the gold grains of Comparative Example is shown in FIG. 8, and a distribution of the aspect ratios of the gold grains of Comparative Example is indicated in FIG. 9. As is apparent from FIG. 8, the tin oxide layer of Comparative Example was partially exposed to the outside through gaps among the gold grains. The gold grains of Comparative Example were of varying three-dimensional shapes but generally round in shape as is seen in FIG. 8. In Comparative Example, the percentage of non-spherical gold grains having an aspect ratio of 2.0 or greater was about 1%, and the percentage of spherical gold grains having an aspect ratio of smaller than 1.1 was about 30%.

A variation in the sensor response Rg/Ra with respect to the energization time is indicated in FIG. 10. As is apparent from FIG. 10, the sensor response Rg/Ra was lowered by about 3.5 during a lapse of 300 hours after the initiation of energization in Comparative Example.

Figure 13:
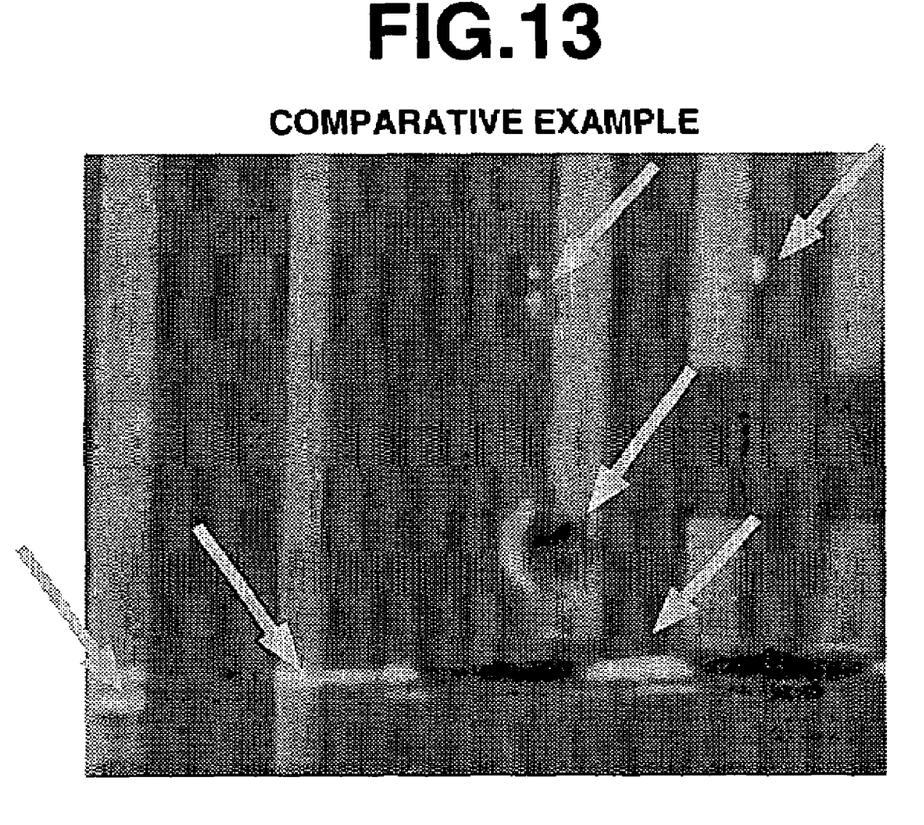
FIG. 13 is an optical microscope photograph of the sensor element of Comparative Example.

Further, an optical microscope photograph of the tin oxide layer and the gold grains of Comparative Example is indicated in FIG. 13. In Comparative Example, some separations of the gold grains from the tin oxide layer were observed as indicated by arrows in FIG. 13.

The evaluation results of Comparative Example were also summarized in TABLE 1.

TABLE 1

| | Catalyst Grain Separation | Catalyst Grain Form | Energization Durability | Total Sensor Performance |
|---|---|---|---|---|
| Example 1 | None | Non-spherical (partially flat) | Very good | Excellent |
| Example 2 | None | Non-spherical (partially flat) | Good | Good |
| Comparative Example | Observed | Spherical | Poor | Poor |

As described above, the sensor of Comparative Example had a low percentage of non-spherical gold grains and high percentage of spherical gold grains so that the area of contact between the tin oxide layer and the gold grain was relatively small. There thus occurred some separations of the catalytic gold grains from the gas sensing tin oxide layer due to poor adhesion between the tin oxide layer and the gold grains in Comparative Example. Further, the sensor of Comparative Example had a large amount of deterioration in the sensor response Rg/Ra during the course of energization and was low in durability and stability. The total sensor performance of Comparative Example was rated as "poor" for the reasons mentioned above.

On the other hand, each of the sensors of Examples 1 and 2 had a high percentage of non-spherical gold grains and a low percentage of spherical gold grains so that the area of contact between the tin oxide layer and the gold grains was relatively large. There thus occurred no separation of the catalytic gold grains from the gas sensing tin oxide layer due to good adhesion between the tin oxide layer and the gold grains in Examples 1 and 2. It has been shown that the separation of the catalyst grains from the gas sensing layer can be prevented through the oxygen content control of the heat treatment atmosphere and the aspect ratio control of the catalyst grains. Further, the sensors of Examples 1 and 2 had a small amount of deterioration in the sensor response Rg/Ra during the course of energization and showed excellent durability and highly stable gas sensitivity. The sensor of Example 1, in particular, was superior in point of energization durability. Accordingly, the total sensor performance of Example 1 was rated as "excellent", and the total sensor performance of Example 2 was rated as "good".

EXPERIMENT 2

Seven sample sensors (Sample Numbers 1 to 7) having different catalyst area ratios were produced in the same manner as in Example 1. The catalyst area ratio of each sample sensor was herein controlled by adjusting the amount of gold grains applied to an arbitrary degree and determined, according to the above-defined method, by taking a reflected electron image of the sample by FE-SEM with a magnification of 80,000 times and an acceleration voltage of 5 kV. Further, the sensor response Rg/Ra of each sample sensor was determined in the same manner as in Example 1. The evaluation results are summarized in TABLE 2.

TABLE 2

| Sample Number | Catalyst Area Ratio (%) | Sensor Response Rg/Ra |
|---|---|---|
| 1 | 1 | 1.5 |
| 2 | 2 | 2.5 |
| 3 | 36 | 2.0 |
| 4 | 60 | 3.0 |
| 5 | 72 | 2.5 |
| 6 | 90 | 1.8 |
| 7 | 95 | 1.4 |

All of the sample sensors were usable for gas detection so as to produce output responsive to the gas concentrations as the sensor response Rg/Ra was detected to be larger than 1. When the catalyst area ratio was within the above-specified desirable range of 1.5 to 93.0%, the sensor response Rg/Ra reached a given sensitivity level (e.g. of 1.6 or higher) so as not to cause problems in the use for gas detection even under conditions of sensitivity deterioration. The sensor response Rg/Ra reached a higher level (of 1.8 or higher) when the catalyst area ratio was within the range of 2.0 to 90%, When the catalyst area ratio was within the range of 2.0 to 75.0%, the sensor response Rg/Ra reached a still higher sensitivity level (of 2.0 or higher). It has been thus shown that the gas sensitivity can be improved through the control of the catalyst area ratio.

The entire contents of Japanese Patent Application No. 2005-049295 (filed on Feb. 24, 2005), No. 2005-183171 (filed on Jun. 23, 2005) and No. 2006-003692 (filed on Jan. 11, 2006) are herein incorporated by reference.

Although the present invention has been described with reference to some specific embodiments of the invention, the invention is not limited to the above-described embodiments. Various modification and variation of the embodiments described above will occur to those skilled in the art in light of the above teaching. It is needless to say that the aspect ratio control of the catalyst grains and the oxygen content control of the heat treatment atmosphere is applicable to any other metal oxide semiconductor sensor of the type in which the gas sensing layer is provided in contact with the catalyst portion even when the gas sensor layer and the catalyst portion is of different metal oxide semiconductor and noble metal catalyst materials. The scope of the invention is defined with reference to the following claims.

What is claimed is:

1. An oxidizing gas sensor, comprising:
    an insulating substrate;
    a gas sensing layer laminated on the insulating substrate and substantially made of tin oxide so as to make resistance changes in response to concentration variations in oxidizing gas; and
    a plurality of catalyst grains applied to a surface of the gas sensing layer and substantially made of gold,
    wherein 20% or more of the catalyst grains has an aspect ratio of 2.0 or greater when viewed at from the surface of the gas sensing layer, and
    wherein an area of the surface of the gas sensing layer covered by the catalyst grains constitutes 1.5 to 93.0% of the total area of the surface of the gas sensing layer.

2. The oxidizing gas sensor according to claim 1, wherein 10% or less of the catalyst grains have an aspect ratio of smaller than 1.1.

3. The oxidizing gas sensor according to claim 1, wherein at least part of the surface of the gas sensing layer is exposed to the outside of the gas sensor and the catalyst grains are at least partially exposed to the outside of the gas sensing layer.

4. The oxidizing gas sensor according to claim 1, wherein at least some of the catalyst grains are at least partially flat in shape.

5. The oxidizing gas sensor according to claim 1, wherein the ratio of the number of gold atoms to the number of gold and tin atoms at the surface of the gas sensing layer falls within a range of 10 to 70%.

6. The oxidizing gas sensor according to claim 1,
the insulating substrate having a substrate core and an insulating layer laminated on the substrate core to support thereon the gas sensing layer,
the substrate core defining therein an opening at a location corresponding to the gas sensing layer, and
the gas sensor further comprising a heater embedded in the insulating film, at a location corresponding to the gas sensing layer and the opening so as to heat the gas sensing layer.

7. A method for producing an oxidizing gas sensor, comprising:
an insulating substrate;
a gas sensing layer laminated on the insulating substrate and substantially made of tin oxide so as to make resistance changes in response to concentration variations in oxidizing gas; and
a plurality of catalyst grains applied to a surface of the gas sensing layer and substantially made of gold,
wherein 20% or more of the catalyst grains has an aspect ratio of 2.0 or greater when viewed at from the surface of the gas sensing layer, and wherein an area of the surface of the gas sensing layer covered by the catalyst grains constitutes 1.5 to 93.0% of the total area of the surface of the gas sensing layer,
said method comprising:
forming a gas sensing layer of tin oxide on an insulating substrate by a thin-film formation process;
applying, without adding heat to the insulating substrate, catalyst grains of gold to a surface of the gas sensing layer by a thin-film application process; and
heat treating the gas sensing layer and the catalyst grains in an atmosphere with an oxygen content of 10 ppm or lower.

8. The method according to claim 7, wherein the heat treating includes agglomerating the catalyst grains in such a manner that 20% or more of the catalyst grains have an aspect ratio of 2.0 or greater when viewed at from the surface of the gas sensing layer.

9. An oxidizing gas sensor, comprising:
an insulating substrate;
a gas sensing layer laminated on the insulating substrate and substantially made of tin oxide so as to make resistance charges in response to concentration variations in oxidizing gas; and
a plurality of catalyst grains applied to a surface of the gas sensing layer and substantially made of gold,
wherein 20% or more of the catalyst grains has an aspect ratio of 2.0 or greater when viewed at from the surface of the gas sensing layer; and 10% or less of the catalyst grains have an aspect ratio of smaller than 1.1.

* * * * *